United States Patent [19]
Cominacini

[11] Patent Number: 6,040,322
[45] Date of Patent: Mar. 21, 2000

[54] MEDICAMENTS FOR AMELIORATING ENDOTHELIAL CELL ACTIVATION

[75] Inventor: Luciano Cominacini, Verona, Italy

[73] Assignee: Glaxo Wellcome Inc., Research Triangle Park, N.C.

[21] Appl. No.: 09/194,950

[22] PCT Filed: Jun. 6, 1997

[86] PCT No.: PCT/GB97/01521

§ 371 Date: Dec. 9, 1998

§ 102(e) Date: Dec. 9, 1998

[87] PCT Pub. No.: WO97/46238

PCT Pub. Date: Dec. 11, 1997

[30] Foreign Application Priority Data

Jun. 7, 1996 [GB] United Kingdom .................. 9611947

[51] Int. Cl.⁷ .................................................. A61K 31/425
[52] U.S. Cl. .......................................... 514/370; 514/369
[58] Field of Search ...................... 514/369, 370

[56] References Cited

U.S. PATENT DOCUMENTS 5,594,015  1/1997  Kurtz et al. .
5,824,694  10/1998  Kurtz et al. .

FOREIGN PATENT DOCUMENTS 0 139 421  5/1985  European Pat. Off. .
0 312 913  4/1989  European Pat. Off. .
0 319 288  6/1989  European Pat. Off. .
WO 94 19347  9/1994  WIPO .
WO 95 07697  3/1995  WIPO .
WO 95/35108  12/1995  WIPO .

OTHER PUBLICATIONS

Law: "Troglitazone inhibits vascular smooth muscle cell growth and intimal hyperplasia", J. Clin. Invest., vol. 98, No. 8, Oct. 15, 1996, pp. 1897–1905.

Pober: "Cytokine–mediated activation of vascular endothelium", Am. J. Pathol., vol. 133, No. 8, 1988, pp. 426–433.

*Primary Examiner*—Raymond Henley, III
*Attorney, Agent, or Firm*—Robert H. Brink

[57] ABSTRACT

The use of compound of formula (I) in which: $R^1$ and $R^2$ are the same or different and each represents a hydrogen atom or a $C_1$–$C_5$ alkyl group; $R^3$ represents a hydrogen atom, a $C_1$–$C_6$ aliphatic acyl group, a ($C_5$–$C_7$ cycloalkane) carbonyl group, an aromatic acyl group which is a benzoyl or naphthoyl group optionally with one or more nitro, amino, alkylamino, dialkylamino, alkoxy, halo, alkyl or hydroxy substituents, a heterocyclic acyl group having one or more oxygen, sulphur or nitrogen hetero atoms and with 4 to 7 ring atoms, an optionally halo-substituted phenylacetyl or phenylpropionyl group, a cinnamoyl group, a ($C_1$–$C_6$ alkoxy) carbonyl group or a benzolyloxycarbonyl group; $R^4$ and $R^5$ are the same or different and each represents a hydrogen atom, a $C_1$–$C_5$ alkyl group or a $C_1$–$C_5$ alkoxy group, or $R^4$ and $R^5$ together represent a $C_1$–$C_4$ alkylenedioxy group; n is 1, 2, or 3; W represents the —$CH_2$, >CO or >CH—$OR^6$ group (in which $R^6$ represents any one of the atoms or groups defined for $R^3$ and may by the same as or different from $R^3$); and Y and Z are the same or different and each represents an oxygen atom or an imino (=NH) group; or a pharmaceutically acceptable salt thereof, for the manufacture of a medicament for the amelioration of inappropriate endothelial cell activation.

7 Claims, 1 Drawing Sheet

MEDICAMENTS FOR AMELIORATING ENDOTHELIAL CELL ACTIVATION

This application is filed pursuant to 35 U.S.C. § 371 as a United States National Phase Application of International Application No. PCT/GB97/01521 filed Jun. 6, 1997, which claims priority from GB 9611947.4 filed Jun. 7, 1996.

The present invention relates to the use of thiazolidine derivatives for ameliorating endothelial cell activation.

European patent no. 0139421 describes thiazolidine derivatives of formula (I):

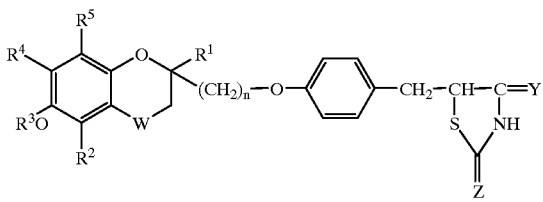

in which:
- $R^1$ and $R^2$ are the same or different and each represents a hydrogen atom or a $C_1$–$C_5$ alkyl group;
- $R^3$ represents a hydrogen atom, a $C_1$–$C_6$ aliphatic acyl group, a ($C_5$–$C_7$ cycloalkane) carbonyl group, an aromatic acyl group which is a benzoyl or naphthoyl group optionally with one or more nitro, amino, alkylamino, dialkylamino, alkoxy, halo, alkyl or hydroxy substituents, a heterocyclic acyl group having one or more oxygen, sulphur or nitrogen hetero atoms and with 4 to 7 ring atoms, an optionally halo-substituted phenylacetyl or phenylpropionyl group, a cinnamoyl group, a ($C_1$–$C_6$ alkoxy) carbonyl group or a benzoyloxycarbonyl group;
- $R^4$ and $R^5$ are the same or different and each represents a hydrogen atom, a $C_1$–$C_5$ alkyl group or a $C_1$–$C_5$ alkoxy group, or $R^4$ and $R^5$ together represent a $C_1$–$C_4$ alkylenedioxy group;
- n is 1, 2 or 3;
- W represents the —$CH_2$—, >CO or >CH—$OR^6$ group (in which $R^6$ represents any one of the atoms or groups defined for $R^3$ and may be the same as or different from $R^3$); and
- Y and Z are the same or different and each represents an oxygen atom or an imino (=NH) group;

and pharmaceutically acceptable salts thereof.

The compounds are said to show blood lipid metabolism ameliorating activity and to have the ability to decrease the levels of blood lipid peroxides, blood triglycerides and blood cholesterol.

International patent application publication no. WO94/19347 describes the ability of compounds of formula (I) to inhibit the oxidation and/or peroxidation of low density lipoprotein (LDL) and suggest that the compounds may therefore have utility in the treatment of arteriosclerosis.

We have now surprisingly found that compounds of formula (I) reduce the activation of endothelial cells and are therefore useful in the treatment of disorders associated with endothelial cell activation.

The vascular endothelium maintains a non-thrombogenic surface on the inside of blood vessels, regulates the growth and differentiation of underlying tissues and plays a pivotal role in controlling trafficking of leukocytes in inflammatory conditions. Perturbations in endothelial functioning are implicated in many diseases, including atherosclerotic and inflammatory diseases.

Activation of the endothelial cell in post-capillary venules leads to increased expression of adhesion molecules and consequent recruitment of blood leukocytes into adventitial tissue. Whilst this is a necessary step in the physiological defence mechanisms to foreign bodies, inappropriate endothelial cell activation is implicated in pathological inflammatory states.

The activation state of endothelial cells is at least in part determined by the effect of so-called inflammatory mediators, such as TNFα, interieukin-1. These agents are secreted by inflammatory cells, and cause activation of endothelial cells. A typical response of endothelial cells to such activation is to increase expression of adhesion molecules on the cell surface which allows recruitment of blood leukocytes to sites of inflammation. Therefore the level of adhesion molecules on the surface of endothelial cells can be taken as a measure of activation of the cells under inflammatory stimulus.

Such endothelial cell activation is also thought to be the initiating event for atherosclerotic cardiovascular disease. These arterial plaques contain macrophages and lymphocytes recruited from plasma by adhesion molecules on the endothelial cell surface. The macrophages in particular have been implicated in the acute symptoms (such as angina pectoris, myocardial infarction) associated with atherosclerotic plaques.

In a first aspect, the present invention provides the use of a compound of formula (I):

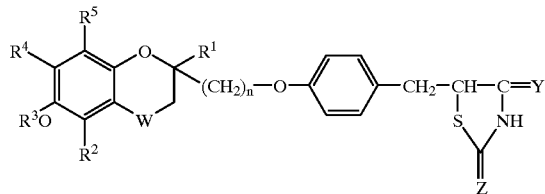

in which:
- $R^1$ and $R^2$ are the same or different and each represents a hydrogen atom or a $C_1$–$C_5$ alkyl group;
- $R^3$ represents a hydrogen atom, a $C_1$–$C_6$ aliphatic acyl group, a ($C_5$–$C_7$ cycloalkane) carbonyl group, an aromatic acyl group which is a benzoyl or naphthoyl group optionally with one or more nitro, amino, alkylamino, dialkylamino, alkoxy, halo, alkyl or hydroxy substituents, a heterocydic acyl group having one or more oxygen, sulphur or nitrogen hetero atoms and with 4 to 7 ring atoms, an optionally halo-substituted phenylacetyl or phenylpropionyl group, a cinnamoyl group, a ($C_1$–$C_6$ alkoxy) carbonyl group or a benzoyloxycarbonyl group;
- $R^4$ and $R^5$ are the same or different and each represents a hydrogen atom, a $C_1$–$C_5$ alkyl group or a $C_1$–$C_5$ alkoxy group, or $R^4$ and $R^5$ together represent a $C_1$–$C_4$ alkylenedioxy group;
- n is 1, 2 or 3;
- W represents the —$CH_2$, >CO or >CH—$OR^6$ group (in which $R^6$ represents any one of the atoms or groups defined for $R^3$ and may be the same as or different from $R^3$); and
- Y and Z are the same or different and each represents an oxygen atom or an imino (=NH) group;

or a pharmaceutically acceptable salt thereof, for the manufacture of a medicament for the amelioration of inappropriate endothelial cell activation.

In a second or alternative aspect, the invention provides a method for the treatment of an animal, including man, suffering from inappropriate endothelial cell activation, which method comprises administration of a therapeutically effective amount of a compound of formula (I) or a pharmaceutically acceptable salt thereof.

As will be appreciated by those skilled in the art, references herein to treatment extend to prophylaxis as well as to the treatment of established disorders or symptons thereof.

In a preferred aspect, the present invention provides the use of a compound of formula (I) or a pharmaceutically acceptable salt thereof for the manufacture of a a medicament for the amelioration of endothelial cell activation in atherosclerotic cardiovascular disease, including angina, myocardial infarction, peripheral vascular disease and cerebrovascular disease.

The invention further provides a method for the amelioration of endothelial cell activation in an animal, including man, suffering from atherosclerotic cardiovascular disease, including angina, myocardial infarction, peripheral vascular disease and cerebrovascular disease which method comprises administration of an effective amount of a compound of formula (I) or a pharmaceutically acceptable salt thereof.

In a further preferred aspect, the present invention provides the use of a compound of formula (I) or a pharmaceutically acceptable salt thereof for the manufacture of a medicament for the treatment of an inflammatory disorder associated with inappropriate endothelial cell activation.

The invention further provides a method for the treatment of an animal, including man, suffering from an inflammatory disorder associated with inappropriate endothelial cell activation, which method comprises administration of an effective amount of a compound of formula (I) or a pharmaceutically acceptable salt thereof.

Figure 1:
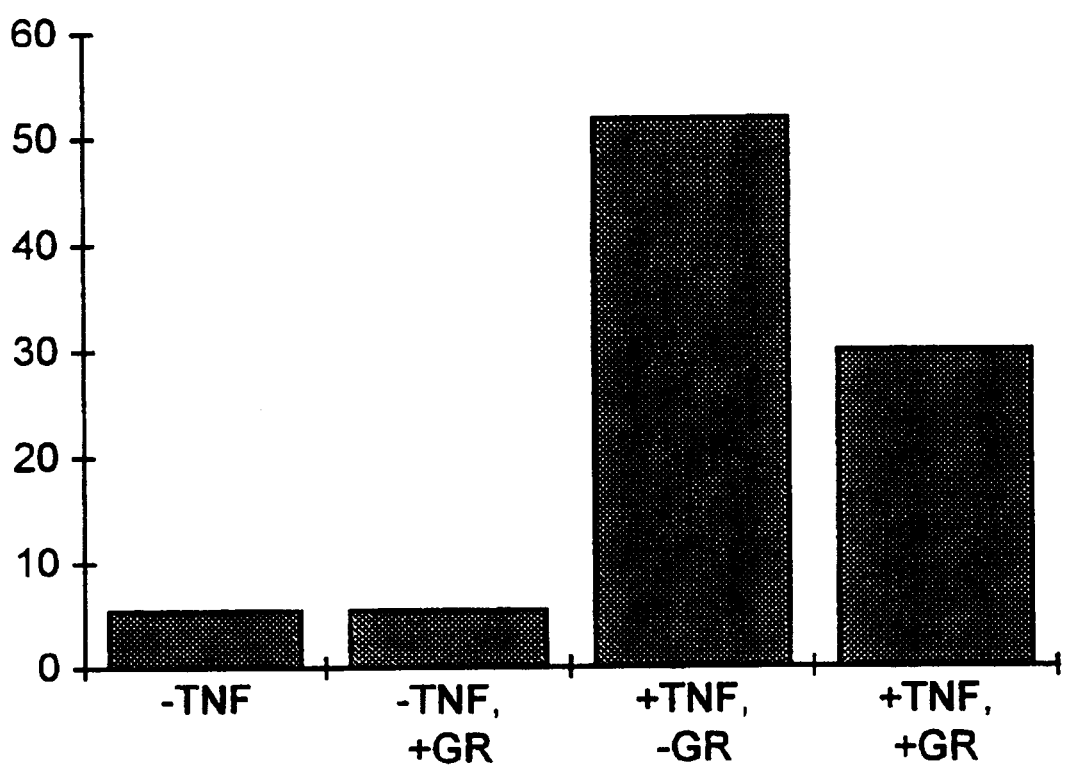
FIG. 1 ("FIG 1") summarizes the effects of troglitazone on TNF-induced VCAM expression on HUVECS. The test method is described on pages 11 and 12 below.

Inflammatory disorders associated with inappropriate endothelial cell activation include, for example, rheumatoid arthritis; systemic lupus erythamatosis; renal diseases including glomerulonephritis; hypertension and complications thereof; tissue reperfusion damage; adult respiratory distress syndrome; radiation-induced injuries; burns; inflammation in asthma, influenza and chronic bronchitis; inflammatory diseases of the gastrointestinal tract such as Crohn's disease, ulcerative colitis, inflammatory bowel disease, non-steroidal anti-inflammatory drug induced damage and inflammatory and secretory effects of bacterial infection, e.g. due to *Clostridium difficile*; inflammatory diseases of the skin such as herpes and eczema; inflammatory diseases of the bladder such as cystitis and urge (i.e. urinary) incontinence; eye and dental inflammation, e.g. gingivitis and periodontitis; and neurodegenerative diseases such as Alzheimer's disease.

It will be appreciated by those skilled in the art that formula (I) is intended to include all stereoisomers, including enantiomers and diastereoisomers, and mixtures thereof including racemates.

In compounds of formula (I) it is preferred that:

$R^1$ represents $C_{1-4}$alkyl;

$R^2$ represents H or $C_{1-3}$akyl;

$R^3$ represents H, $C_{1-4}$aliphatic acyl, unsubstituted $C_{7-11}$ aromatic acyl or $C_{2-4}$alkoxycarbonyl;

$R^4$ represents $C_{1-4}$alkyl; and $R^5$ represents H or $C_{1-3}$alkyl.

More preferably $R^3$ represents H, acetyl, benzoyl or ethoxycarbonyl.

Most preferably:

$R^1$ represents methyl;

$R_2$ represents H or methyl;

$R^3$ represents H, acetyl or ethoxycarbonyl;

$R^4$ represents methyl or t-butyl; and $R^5$ represents H or methyl.

A particularly preferred compound for use in accordance with the present invention is 5-[4-(6-hydroxy-2,5,7,8-tetramethylchroman-2-ylmethoxy) benzyl]thiazolidine-2,4-dione, represented by formula (IA):

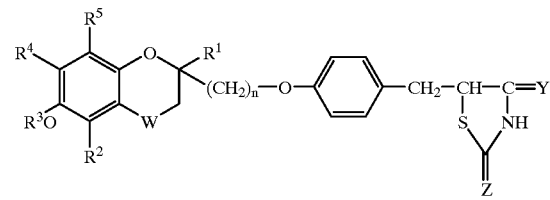

The compound of formula (IA) is also known as troglitazone.

Compounds of formula (I) and their pharmaceutically acceptable salts may be prepared as described in EP 0139421.

It will be appreciated that the amount of a compound of formula (I) required for use in treatment according to the invention will vary not only with the particular compound selected but also with the route of administration, the nature of the condition being treated and the age and condition of the patent and will be ultimately at the discretion of the attendant physician or veterinarian. In general however a suitable dose will be in the range of from about 0.5 to about 20 mg/kg of bodyweight per day preferably in the range of 0.1 to 15 mg/kg/day, most preferably in the range of 1 to 10 mg/kg/day, such as about 50–500 mg per day for a normal adult.

The desired dose may conveniently be presented in a single dose or as divided doses administered at appropriate intervals, for example as two, three, four or more sub-doses per day.

The compound is conveniently administered in unit dosage form; for example containing 10 to 800 mg, conveniently 20 to 500 mg, most conveniently 50 to 500 mg of active ingredient per unit dosage form.

While it is possible that, for use in therapy, a compound of the invention may be administered as the raw chemical it is preferable to present the active ingredient as a pharmaceutical formulation.

A pharmaceutical formulation will comprise a compound of formula (I) or a pharmaceutically acceptable derivative thereof together with one or more pharmaceutically acceptable carriers therefor and, optionally, other therapeutic and or/ prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. Oral and parenteral administration are preferred. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary, or paste. Tablets and capsules for oral administration may contain conventional excipients such as binding agents, fillers, lubricants, disintigrants or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles and may contain formulatory agents such as suspending, stabilising and/or dispersing agents. Alternatively, the active ingredient may be in powder form, obtained by a aseptic isolation of sterile solid or by lyophilisation from solution, for constitution with a suitable vehicle e.g. sterile, pyrogen-free water, before use.

For topical administration to the epidermis the combinations according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other commonly used, materials in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, paste, foams or sprays containing in addition to the active ingredient such carriers as are known in the art to be carriers.

For intra-nasal administration the compounds of the invention may be used as a liquid spray or dispersible powder or in the form of drops.

Drops may be formulated with an aqueous or non-aqueous base also comprising one or more dispersing agents, solubilising agents or suspending agents. Liquid sprays are conveniently delivered from pressurised packs.

For administration by inhalation the compounds according to the invention are conveniently delivered from an insulator, nebuliser or a pressure pack or other convenient means of delivering an aerosol spray. Pressurised packs may comprise a suitable propellent such as dichlorodifluoromethane, trichlorofluromethane, dichlorotetrafluoroethane, carbon dioxide or other suitable gas. In the case of a pressurised aerosol the dosage unit may be determined by providing a value to deliver a metered amount.

Alternatively, for administration by inhalation or insufflation, the compounds according to the invention may take the form of a dry powder composition, for example a powder mix compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The pharmaceutical compositions for use in the present invention may also contain other active ingredients such as antimicrobial agents, or preservatives.

The inhibitory effect of the compound of formula (IA) on endothelial cell activation is demonstrated by the following Examples, which are illustrative of the present invention and not limitative thereof.

The invention is further illustrated by the following non-limitative example.

EXAMPLE

Endothelial cells from human umbilical veins (HUVECs) were isolated by conventional methods, maintained in culture and used between passages 2 and 4.

To aid solubility of troglitazone, human low density lipoprotein (isolated by serial density centrifugation) was used as a carrier. 5 $\mu$g of troglitazone was incubated with LDL for 24 h at 4° C. in M-199 medium containing 10% foetal calf serum. Troglitazone containing LDL was purified by gel-filtration and any contaminating endotoxin removed by passing the troglitazone over a pre-packed endotoxin affinity column.

Troglitazone containing LDL was incubated with HUVECs in M-199 medium at 37° C. for 24 h. After this time the troglitazone-containing medium was removed.

The HUVECs were incubated with TNF$\alpha$ (100U/ml, Sigma) in M-199 medium at 37° C. for 24 h. After this time, the level of VCAM-1 on the cell surface was measured using antibody detection in a FACS machine by conventional methods.

The results are presented in FIG. 1.

The presence of troglitazone in the pre-incubation clearly attenuates the expression of the adhesion molecule VCAM-1 in response to the inflammatory mediator TNF$\alpha$.

I claim:

1. A method for the treatment of an animal, including man, suffering from inappropriate endothelial cell activation, which method comprises administration of a therapeutically effective amount of a compound of formula (I):

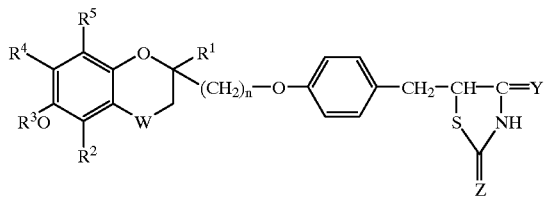

in which:
  R¹ and R² are the same or different and each represents a hydrogen atom or a $C_1$–$C_5$ alkyl group;
  R³ represents a hydrogen atom, a $C_1$–$C_6$ aliphatic acyl group, a ($C_5$–$C_7$ cycloalkane) carbonyl group, an aromatic acyl group which is a benzoyl or naphthoyl group optionally with one or more nitro, amino, alkylamino, dialkylamino, alkoxy, halo, alkyl or hydroxy substituents, a heterocyclic acyl group having one or more oxygen, sulphur or nitrogen hetero atoms and with 4 to 7 ring atoms, an optionally halo-substituted phenylacetyl or phenylpropionyl group, a cinnamoyl group, a ($C_1$–$C_6$ alkoxy) carbonyl group or a benzoyloxycarbonyl group;
  R⁴ and R⁵ are the same or different and each represents a hydrogen atom, a $C_1$–$C_5$ alkyl group or a $C_1$–$C_5$ alkoxy group, or R⁴ and R⁵ together represent a $C_1$–$C_4$ alkylenedioxy group;
  n is 1, 2 or 3;
  W represents the —$CH_2$, >CO or >CH—OR⁶ group (in which R⁶ represents any one of the atoms or groups defined for R³ and may be the same as or different from R³); and
  Y and Z are the same or different and each represents an oxygen atom or an imino (=NH) group;
or a pharmaceutically acceptable salt thereof.

2. The method according to claim 1 wherein;
  R¹ represents $C_{1-4}$ alkyl;
  R² represents H or $C_{1-3}$ alkyl;
  R3 represents H, $C_{1-4}$ aliphatic acyl, unsubstituted $C_{7-11}$ aromatic acyl or $C_{2-4}$ alkoxcarbonyl;
  R⁴ represents $C_{1-4}$ alkyl and
  R⁵ represents $C_{1-3}$ alkyl
or a pharmaceutically acceptable salt thereof.

3. The method according to claim 2 wherein R³ represents H, acetyl, benzoyl or ethoxycarbony, or a pharmaceutically acceptable salt thereof.

4. The method according to claim 2 wherein;
  R¹ represents methyl;
  R² represents H or methyl;
  R³ represents H, acetyl or ethoxycarbonyl
  R⁴ represents methyl or t-butyl and
  R⁵ represents H or methyl,
or a pharmaceutically acceptable salt thereof.

5. The method according to claim 1 where the compound is troglitazone.

6. The method of claim 1 wherein said endothelial cell activation is in atherosclerotic cardiovascular disease.

7. The method of claim 1 wherein said method is for the treatment of an inflammatory disorder associated with inappropriate endothelial cell activation.

* * * * *